US007153953B2

(12) United States Patent
Marraccini et al.

(10) Patent No.: US 7,153,953 B2
(45) Date of Patent: Dec. 26, 2006

(54) LEAF SPECIFIC GENE PROMOTER OF COFFEE

(75) Inventors: Pierre Marraccini, Savonnières (FR); John Rogers, St Genis Pouilly (FR)

(73) Assignee: Nestec S.A., Vevey (CH)

( * ) Notice: Subject to any disclaimer, the term of this patent is extended or adjusted under 35 U.S.C. 154(b) by 123 days.

(21) Appl. No.: 10/477,307

(22) PCT Filed: Mar. 27, 2002

(86) PCT No.: PCT/EP02/03469

§ 371 (c)(1),
(2), (4) Date: Jun. 7, 2004

(87) PCT Pub. No.: WO02/092822

PCT Pub. Date: Nov. 21, 2002

(65) Prior Publication Data

US 2004/0244072 A1    Dec. 2, 2004

(30) Foreign Application Priority Data

May 11, 2001    (EP)    .................................. 01111573

(51) Int. Cl.
C07H 21/04    (2006.01)
C12N 9/88    (2006.01)
C12N 15/00    (2006.01)
C12N 5/04    (2006.01)
A01H 5/00    (2006.01)

(52) U.S. Cl. .................... 536/24.1; 536/23.6; 536/23.2; 435/232; 435/320.1; 435/419; 800/298

(58) Field of Classification Search ............... 536/24.1, 536/23.2, 23.6; 435/232, 320.1, 419; 800/298, 800/205
See application file for complete search history.

(56) References Cited

FOREIGN PATENT DOCUMENTS

| EP | 0 894 865 A2 | 2/1999 |
| WO | WO 98/36053 | 8/1998 |
| WO | WO 99/02688 | 1/1999 |

OTHER PUBLICATIONS

Baker et al. article entitled "The Structure Of Form I Crystals Of D-Ribulose-1, 5-Diphosphate Carboxylase", J. Mol. Biol., Feb. 5, 1975, 91(4), 391-399.
Bevan article entitled "Binary Agrobacterium Vectors For Plant Transformation", Nucl. Acids Res., Oct. 1984, 12, 8711-8721.
Bjellqvist et al. entitled "A Nonlinear Wide-Range Immobilized pH Gradient For Two-Dimensional Electrophoresis And Its Definition In A Relevant pH Scale", Electrophoresis, Dec. 1993, 14(12), 1357-1365.
Bradford article entitled "A Rapid And Sensitive Method For The Quantitation Of Microgram Quantities Of Protein Utilizing The Principle Of Protein-Dye Binding", Anal. Biochem. May, 1976, 72, 248-254.
Damerval et al. article entitled "Technical Improvements in Two-Dimensional Electrophoresis Increase The Level of Genetic Variation Detected in Wheat-Seedling Proteins", Electrophoresis, 1986, 7, 52-54.
Dean et al. article entitled "Structure, Evolution, and Regulation of RbcS Genes in Higher Plants", Annu. Rev. Plant Physiol. Plant Mol. Biol., Jun. 1989, vol. 40, pp. 415-439.
Herrera et al. article entitled "Evolution Of Light-Regulated Plant Promoters", Annu. Rev. Plant Physiol. Plant Mol. Biol., Jun. 1998, 49, 525-555.
Horsch et al., article entitled "Leaf Disc Transformation", Plant Mol. Biol. Manuel, Gelvin, Schilperoort and Verma Eds, Kluwer Academic Publishers Dordrecht, Netherlands, 1993, A5, 1-9.
Jefferson et al. article entitled "GUS Fusions: Beta-Glucuronidase As A Sensitive And Versatile Gene Fusion Marker In Higher Plants", EMBO J., Dec. 20, 1987, 6(13), 3901-3907.
Lundberg et al. article entitled "High-fidelity amplification using a thermostable DNA polymerase isolated from Pyrococcus furiosus," Gene, 1991, 108(1991)1-6.
Migge et al. article entitled "Leaf-Specific Overexpression of Plastidic Glutamine Synthetase Stimulates The Growth of Transgenic Tobacco Seedlings", Planta, Jan. 2000, 210(2), 252-260.
Murashige and Skoog article entitled "A Revised Medium For Rapid Growth And Bio Assays With Tobacco Tissue Cultures", Physiol. Plant 15, 1962, 473-497.
Ochman et al. article entitled "Genetic Applications Of An Inverse Polymerase Chain Reaction", Genetics, Nov. 1988, 120, 621-623.
Paillard et al. article entitled "Construction Of A Molecular Linkage Map In Coffee", Theor. Appl. Genet, Jul. 1996, 93, 41-47.
R.T. Fraley et al. article entitled "Expression Of Bacterial Genes In Plant Cells", Proc. Natl. Acad. Sci., Aug. 1983, 80, 4803-4807.
Rogers and Bendich, article entitled "Extraction of DNA from Plant Tissues", Plant Mol. Biol. Manuel, Gelvin, Schilpoort and Verma Eds, Kluwer Adademic Publishers Dordrecht, Netherlands, 1993, A6, 1-11.
Rogers et al. article entitled "Biochemical And Molecular Characterization And Expression Of The 11S-Type Storage Protein From Coffea Arabica Endosperm", Plaint Physiol. Biochem., Apr. 1999, vol. 37, Issue 4, 261-272.
Smith et al. article entitled "Light-Stimulated Accumulation Of Transcripts Of Nuclear And Chloroplast Genes For Ribulosebisphosphate Carboxylase", J. Mol. Appl. Genet, 1981, 1 (2), 127-137.
Southern article entitled Detection Of Specific Sequences Among DNA Fragments Separated By Gel Electrophoresis, J. Mol. Biol., Nov. 5, 1975, 98, 503-517.

(Continued)

Primary Examiner—Rebecca E. Prouty
Assistant Examiner—Malgorzata Walicka
(74) Attorney, Agent, or Firm—Bell Boyd & Lloyd LLC

(57) ABSTRACT

The present invention relates to a nucleotide sequence derived form coffee leaves that may be used as a promoter for an inducible expression of genes in plants. In particular, the present invention pertains to a nucleotide sequence embracing the promoter and the coding region of a rbcS gene. In addition the present invention relates to transgenic plants containing such recombinant nucleotide sequences.

11 Claims, 3 Drawing Sheets

OTHER PUBLICATIONS

Figure 2:
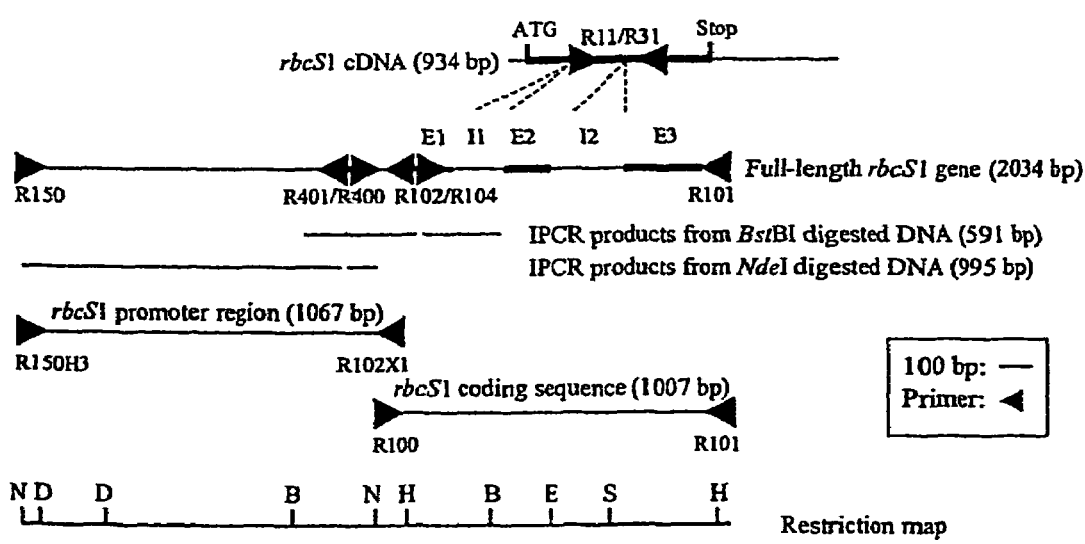

U.K. Laemmli article entitled "Cleavage of Structural Proteins during the Assembly of the Head of Bacteriophage T4," Nature, Aug. 15, 1970, vol. 227, 680-685.

Worrel et al article entitled "Expression Of A Maize Sucrose Phosphate Synthase In Tomato Alters Leaf Carbohydrate Partioning", The Plant Cell, Oct. 1991, vol. 3, 1121-1130.

Laporte et al. article entitled "Promoter strength and tissue specificity effects on growth of tomato plants transformed with maize sucrose-phosphate synthase" *Planta* (2001) 212:pp. 817-822.

Nomura et al. article entitled "The promoter of *rbcS* in a C3 plant (rice) directs organ-specific, light-dependent expression in a C4 plant (maize), but does not confer bundle sheath cell-specific expression" *Plant Molecular Biology* 44:pp. 99-106, 2000.

Kanechi et al. article entitled "Non-Stomatal Inhibition Associated with Inactivation of Rubisco in Dehydrated Coffee Leaves under Unshaded and Shaded Conditions" *Plant Cell Physiol*, 37(4):pp. 455-460 (1996).

Ramalho et al. article entitled "High Irradiance Impartments on Photosynthetic Electron Transport, Ribulose-1,5-bisphosphate Carboxylase/oxygenase and N Assimilation as a Function of N Availability in *Coffea Arabica* L. Plants" *J. Plant Physiol*. vol. 154, pp. 319-326 (1999).

Figure 1

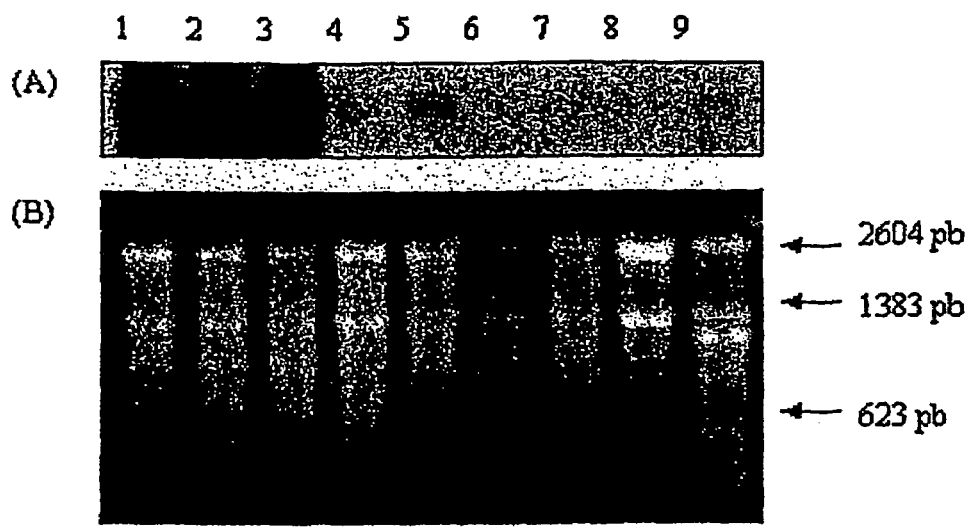

Legend:

(A): Northern-blot analysis of total RNA (20 µg) from various coffee tissue probed with the internal rbcS cDNA.

(B) Total RNA preparations separated by agarose gel electrophoresis and coloured by Ethidium Bromide. Molecular weights are also indicated by arrows.

Lane 1: young leaves (length <5 cm); Lane 2: medium leaves (length >5 cm and < 10 cm); Lane 3: old leaves (length >10 cm); Lane 4: mature flowers; Lane 5: flower buds; Lane 6: stems; Lane 7: roots; Lane 8: mature grains at 35 weeks after flowering; Lane 9: somatic embryons of C. arabica.

Figure 3 Southern-Blot
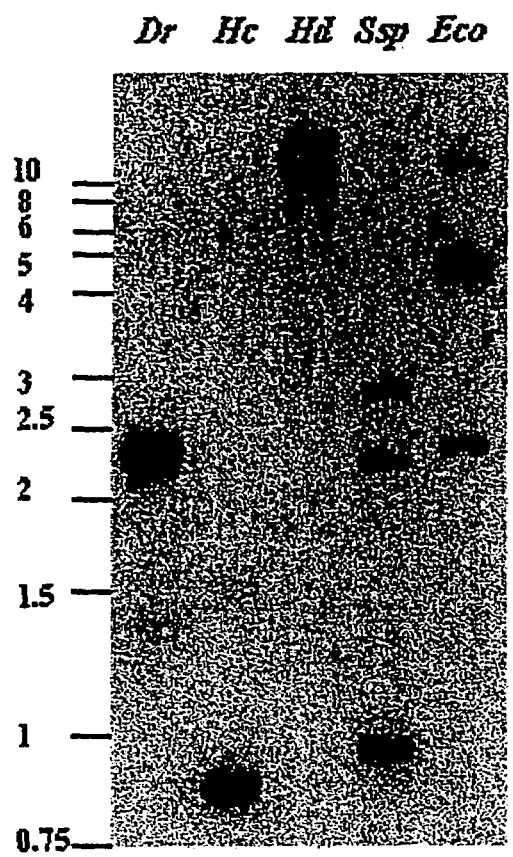
Southern-blot of *C. arabica* genomic DNA digested with *Dra*I (lane *Dr*), *Hinc*II (lane *Hc*), *Hind*III (lane *Hd*), *Ssp*I (lane *Ssp*) and *Eco*RI (lane *Eco*) restriction enzymes and hybridised with the *rbcS1* gene. Molecular length markers (kbp) are also indicated at the left side of the blot.

SEQUENCE LISTING

<160> NUMBER OF SEQ ID NOS: 20

<210> SEQ ID NO 1
<211> LENGTH: 2034
<212> TYPE: DNA
<213> ORGANISM: Coffea arabica

<400> SEQUENCE: 1
catatggaaa ttaatatgca tcaatccttc tctctctctt tttaaaaaaa attaagtttt    60
atatgtcttc ttcactcctt taatgttgca attagcttgt aaggtaaggt tgtgggaag    120 atatatggat agttgtcgga ggaacaattt ttttttttt ttgagacaat aacaattgta    180
taacctattt tatcctaaac tatatagaat agggagtcta aagaaactcg tgttaggaac    240
taacagatac acagacctta ctaaattaaa gagatatttt gacaccactt ttaaattttg    300

-continued

| | |
|---|---|
| ttcactgcag gtgaaatttg agcccctaca taacatacac aggtccctcc ttgacaatca | 360 |
| acgagccaag ctccgtggtt tgttggagga acaattatga aaataaggaa ggcaacggcc | 420 |
| atcacaccag agtctatgtc cgtccagaaa tgtactgaag aacaatgatg tagcaaataa | 480 |
| aatatcttaa gaaaacgata agtttactcc atacatttga gtctgagcaa gggaatggcg | 540 |
| atcgcagaag gaaaagaccg cgacatttct gcactgtagc tgctgcagta tgattctggg | 600 |
| ctcgaaaacg aaatcaaaga atttttattt ttatttttttt tgtgttttgg gtttgaaaaa | 660 |
| aagatatatc gactggaccc aaaattaacc aaccgttact tatcatcctt cgattcacgt | 720 |
| ccttccattc attcgaaaaa cagatgagat aagatgattg aaaatcaatc gccacgtggc | 780 |
| agtgcgagtg tggtggttaa tgataaggct aaggtccaaa accttgtgc cttcatgtgg | 840 |
| tcattaagta gggaatgtgg tgaaccacat aatccaatgg cggacgatgg tctaagatca | 900 |
| ggatgatgga ttttgcccg ttagatacag gaaccatgga agagcaagta gttgcattat | 960 |
| atatagaaag ggttctgtag agcaaaggcc atatgattga ttcccttgct gttattagaa | 1020 |
| gaaaaaagga agggaacgag ctagcgagaa tggcatcctc aatgatctcc tcggcagctg | 1080 |
| ttgccaccac caccagggcc agccctgctc aagctagcat ggttgcaccc ttcaacggcc | 1140 |
| tcaaagccgc ttcttcattc cccatttcca agaagtccgt cgacattact tcccttgcca | 1200 |
| ccaacggtgg aagagtccag tgcatgcagg tacccacac caaccgcaaa atactagcac | 1260 |
| tctctctcta tatatgtaca tgtatgcatt caacttggat ttccactcga gtttgattcg | 1320 |
| aacacacaca cacacacttt taattttagg tgtggccacc aagggactg aagaagtacg | 1380 |
| agactttgtc atatcttcca gatctcaccg acgagcaatt gctcaaggaa attgattacc | 1440 |
| ttatccgcag tggatgggtt ccttgcttgg aattcgagtt ggaggtaaaa aaaaaaaaaa | 1500 |
| aaggttacac agataagatg tttgcatgta ctaacatatt attttttcagt ggcggaaaga | 1560 |
| tttatacaaa caaacaaata aaagggtat agagacaggc attttaatatt tatactgaag | 1620 |
| ctaatacgtt cgtttggtta atgttaatag cagtagagta gagtagatag attaatatgc | 1680 |
| tgatgcgggg tttgtgattt ggtgggtttg aacgtgtaga aaggattgtg gtaccgtgaa | 1740 |
| taccacaggt caccgggata ctatgacgga cgctactgga ccatgtggaa gctgcctatg | 1800 |
| tacggctgca cggacgcaac tcaggtgctg aacgaggttg gggaatgcct gaaggaatac | 1860 |
| ccaaattgct gggtcaggat catcggattc gacaacgtcc gtcaggtgca gtgcatcagt | 1920 |
| ttcattgccg ccaagccaaa gggtttctaa gcccttctt cacaaatttg gccccggccc | 1980 |
| ctcaaatttg aggctgcgat tcttggcagt tgacagttag ttgtcaataa aatt | 2034 |

<210> SEQ ID NO 2
<211> LENGTH: 934
<212> TYPE: DNA
<213> ORGANISM: Coffea arabica

<400> SEQUENCE: 2

| | |
|---|---|
| atttccttgc tgttattaga agaaaaaagg aagggaacga gctagcgaga atggcatcct | 60 |
| caatgatctc tcggcagct gttgccacca ccaccagggc cagccctgct caagctagca | 120 |
| tggttgcacc cttcaacggc ctcaaagccg cttcttcatt ccccatttcc aagaagtccg | 180 |
| tcgacattac ttcccttgcc accaacggtg gaagagtcca gtgcatgcag gtgtggccac | 240 |
| caagggggact gaagaagtac gagactttgt catatcttcc agatctcacc gacgagcaat | 300 |
| tgctcaagga aattgattac cttatccgca gtggatgggt tccttgcttg gaattcgagt | 360 |
| tggagaaagg atttgtgtac cgtgaatacc acaggtcacc gggatactat gacggacgct | 420 |

```
actggaccat gtggaaactg cctatgtacg gctgcacgga cgcaactcaa gtgctgaacg    480
aggttgggga atgcctgaag gaataccoaa attgctgggt caggatcatc ggattcgaca    540
acgtccgtca ggtgcagtgc atcagtttca ttgccgccaa gccaaagggt ttctaagccc    600
cttcttcaca aatttggccc cggcccctca aatttgaggc tgcgattctt ggcagttgac    660
agttagttgt caataaaatt gagaactggg gctgtacttt tagctgtttt tcatttttat    720
ttgccttttc cgtggtggtc tggttttgct tctattcttc tcctttcttt ttttccgctt    780
tgtcattcgg tttcggtata tgtttccgga tttccaaaga tatgtatgag acttttaata    840
atgaaagccg ctttatattc gtctgctacg ctaaaaaaaa aaaaaaaaaa aaaaaaaaa    900 aaaaaaaaa aaaaaaaaaa aaaaaaaaaa aaaa                                934

<210> SEQ ID NO 3
<211> LENGTH: 181
<212> TYPE: PRT
<213> ORGANISM: Coffea arabica

<400> SEQUENCE: 3

Met Ala Ser Ser Met Ile Ser Ser Ala Ala Val Ala Thr Thr Thr Arg
1               5                   10                  15

Ala Ser Pro Ala Gln Ala Ser Met Val Ala Pro Phe Asn Gly Leu Lys
            20                  25                  30

Ala Ala Ser Ser Phe Pro Ile Ser Lys Lys Ser Val Asp Ile Thr Ser
        35                  40                  45

Leu Ala Thr Asn Gly Gly Arg Val Gln Cys Met Gln Val Trp Pro Pro
    50                  55                  60

Arg Gly Leu Lys Lys Tyr Glu Thr Leu Ser Tyr Leu Pro Asp Leu Thr
65                  70                  75                  80

Asp Glu Gln Leu Leu Lys Glu Ile Asp Tyr Leu Ile Arg Ser Gly Trp
                85                  90                  95

Val Pro Cys Leu Glu Phe Glu Leu Glu Lys Gly Phe Val Tyr Arg Glu
            100                 105                 110

Tyr His Arg Ser Pro Gly Tyr Tyr Asp Gly Arg Tyr Trp Thr Met Trp
        115                 120                 125

Lys Leu Pro Met Tyr Gly Cys Thr Asp Ala Thr Gln Val Leu Asn Glu
    130                 135                 140

Val Gly Glu Cys Leu Lys Gly Tyr Pro Asn Cys Trp Val Arg Ile Ile
145                 150                 155                 160

Gly Phe Asp Asn Val Arg Gln Val Gln Cys Ile Ser Phe Ile Ala Ala
                165                 170                 175

Lys Pro Lys Gly Phe
            180

<210> SEQ ID NO 4
<211> LENGTH: 15
<212> TYPE: PRT
<213> ORGANISM: Coffea arabica
<220> FEATURE:
<221> NAME/KEY: misc_feature
<222> LOCATION: (4)..(4)
<223> OTHER INFORMATION: Xaa can be any naturally occurring amino acid

<400> SEQUENCE: 4

His Gln Val Xaa Pro Pro Arg Gly Leu Lys Lys Tyr Glu Thr Leu
1               5                   10                  15
```

```
<210> SEQ ID NO 5
<211> LENGTH: 6
<212> TYPE: PRT
<213> ORGANISM: Coffea arabica

<400> SEQUENCE: 5

Tyr Trp Thr Met Trp Lys
1               5

<210> SEQ ID NO 6
<211> LENGTH: 17
<212> TYPE: DNA
<213> ORGANISM: artificial sequence
<220> FEATURE:
<223> OTHER INFORMATION: RBC1 primer
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 6
atgcargtnt ggccncc                                               17

<210> SEQ ID NO 7
<211> LENGTH: 18
<212> TYPE: DNA
<213> ORGANISM: Artificial sequence
<220> FEATURE:
<223> OTHER INFORMATION: RBC3 primer
<220> FEATURE:
<221> NAME/KEY: misc_feature
<222> LOCATION: (10)..(10)
<223> OTHER INFORMATION: n is a, c, g, or t

<400> SEQUENCE: 7
yttccacatn gtccarta                                              18

<210> SEQ ID NO 8
<211> LENGTH: 24
<212> TYPE: DNA
<213> ORGANISM: Artificial sequence
<220> FEATURE:
<223> OTHER INFORMATION: RBC11

<400> SEQUENCE: 8
atgcaggtgt ggccaccaag ggga                                       24

<210> SEQ ID NO 9
<211> LENGTH: 25
<212> TYPE: DNA
<213> ORGANISM: Artificial sequence
<220> FEATURE:
<223> OTHER INFORMATION: RBC31

<400> SEQUENCE: 9
ccacatggtc cagtagcgtc cgtca                                      25

<210> SEQ ID NO 10
<211> LENGTH: 30
<212> TYPE: DNA
<213> ORGANISM: Artificial sequence
<220> FEATURE:
<223> OTHER INFORMATION: RBC100

<400> SEQUENCE: 10
```
ggaagggaac gagctagcga gaatggcatc                              30

<210> SEQ ID NO 11
<211> LENGTH: 30
<212> TYPE: DNA
<213> ORGANISM: Artificial sequence
<220> FEATURE:
<223> OTHER INFORMATION: RBC101

<400> SEQUENCE: 11
aattttattg acaactaact gtcaactgcc                              30

<210> SEQ ID NO 12
<211> LENGTH: 30
<212> TYPE: DNA
<213> ORGANISM: Artificial sequence
<220> FEATURE:
<223> OTHER INFORMATION: RBC102

<400> SEQUENCE: 12
acagctgccg aggagatcat tgaggatgcc                              30

<210> SEQ ID NO 13
<211> LENGTH: 29
<212> TYPE: DNA
<213> ORGANISM: Artificial sequence
<220> FEATURE:
<223> OTHER INFORMATION: RBC104

<400> SEQUENCE: 13
cagggccagc cctgctcaag ctagcatgg                               29

<210> SEQ ID NO 14
<211> LENGTH: 28
<212> TYPE: DNA
<213> ORGANISM: Artificial sequence
<220> FEATURE:
<223> OTHER INFORMATION: RBC401

<400> SEQUENCE: 14
aacgggcaaa atccatcat cctgatct                                 28

<210> SEQ ID NO 15
<211> LENGTH: 27
<212> TYPE: DNA
<213> ORGANISM: Artificial sequence
<220> FEATURE:
<223> OTHER INFORMATION: RBC400

<400> SEQUENCE: 15
ggaaccatgg aagagcaagt agttgca                                 27

<210> SEQ ID NO 16
<211> LENGTH: 30
<212> TYPE: DNA
<213> ORGANISM: Artificial sequence
<220> FEATURE:
<223> OTHER INFORMATION: RBC150

<400> SEQUENCE: 16
ggaaattaat atgcatcaat ccttctctct                              30

<210> SEQ ID NO 17
<211> LENGTH: 39
<212> TYPE: DNA

-continued

```
<213> ORGANISM: Artificial sequence
<220> FEATURE:
<223> OTHER INFORMATION: RBC150H3

<400> SEQUENCE: 17
cccaagcttg gaaattaata tgcatcaatc cttctctct                              39

<210> SEQ ID NO 18
<211> LENGTH: 41
<212> TYPE: DNA
<213> ORGANISM: Artificial sequence
<220> FEATURE:
<223> OTHER INFORMATION: RBC102X1

<400> SEQUENCE: 18
ctagtctaga cgaggagatc attgaggatg ccattctcgc t                          41

<210> SEQ ID NO 19
<211> LENGTH: 30
<212> TYPE: DNA
<213> ORGANISM: Artificial sequence
<220> FEATURE:
<223> OTHER INFORMATION: BI104

<400> SEQUENCE: 19
tttgatttca cgggttgggg tttctacagg                                       30

<210> SEQ ID NO 20
<211> LENGTH: 30
<212> TYPE: DNA
<213> ORGANISM: Artificial sequence
<220> FEATURE:
<223> OTHER INFORMATION: BI105

<400> SEQUENCE: 20
ggctcgtatg ttgtgtggaa ttgtgagcgg                                       30
```

LEAF SPECIFIC GENE PROMOTER OF COFFEE

The present invention relates to a nucleotide sequence derived from coffee genomic DNA that may be used as a promoter for an inducible expression of genes in plants. In particular, the present invention pertains to a nucleotide sequence embracing the promoter and the coding region of a rbcS gene. In addition the present invention elates to transgenic plants containing such recombinant nucleotide sequences.

DNA sequences controlling the level of transcription of a particular gene are termed promoters. They provide a binding site for the RNA polymerase which binds thereto and brings about transcription of the structural gene(s) under control thereof resulting in the production of messenger RNA (mRNA), which in turn provides the template for the synthesis of the corresponding polypeptides.

Promoters have been studied in a variety of organisms, such as e.g. viruses, bacteria, animals and also plants. For a given species or type of organism, conserved regions of DNA (consensus sequences) have been found within promoters associated with a variety of structural genes. These regions are believed to be involved in the role played by the promoter in the transcription process.

In the art, there have been many studies for introducing foreign genes into plants and expressing them by means of their own promoters. These assays involved the use of inserting the foreign DNA into the Ti plasmid of *Agrobacterium tumefaciens*, and the introduction thereof into plants (cf. R. T. Fraley et al., Proc. Natl. Acad. Sci., (1983) 80, 4803–4807).

However, these measures to express foreign genes in plants proved to be of limited success only, since the amount of the foreign gene product obtained thereby was rather low. To this end, research has focused to isolate native promoters, that is, promoters contained in the plant itself. These promoters should preferably highly active, i.e. provide a high expression and should additionally be inducible.

Certain polypeptides are known to be highly expressed in plants and have therefore been the subject of extensive studies. One of these polypeptides is the enzyme ribulose-1,5-bisphosphate carboxylase (Rubisco), which is the primary enzyme of the carbon fixation pathway in chloroplasts of plants of the C3 class. The enzyme consists of two major types of polypeptide subunits, the small subunit (rbcS) and the large subunit (rbcL) with the enzyme being composed of eight large and eight small subunits (Baker et al., J. Mol. Biol., 91 (1975), 391–399) encoded respectively by the chloroplastic rbcL gene and the nuclear rbcS gene family (Dean et al., Annu Rev. Plant Physiol. Plant Mol. Biol., 40 (1989) 415–439).

Rubisco is known to accumulate in response to light and studies have shown that there is a corresponding increase in the steady state levels of the rbcS mRNA resulting from an increased transcription of the rbcS gene (Smith et al., J. Mol. Appl. Genet., 1 (1981), 127–137).

The structure of light-regulated rbcS promoters was studied in different plants, such as pea or petunia (cf. Herrera et al., Annu. Rev. Plant Physiol. Plant Mol. Biol., 49 (1998) 525–555). At present it is known that several light-responsive DNA regions binding trans-acting factors are necessary for controlling rbcS gene expression at the transcriptional level. Some of the rbcS promoters isolated so far have been characterized and used to express sucrose phosphate synthase (cf. Worrel et al., Plant Cell 3 (1991), 1121–1130) or glutamine synthase (Migge et al., Planta, 210 (2000), 252–260) in leaves of transgenic plants.

In the art there have also been reports of multiple copies of the rbcS gene in the nuclear DNA of various plant genomes, including petunia, pea or wheat. Since not all of the promoter regions of said enzyme have been studied so far there is still a need for providing additional promoters enabling the skilled person to express foreign genes in a plant.

Hence, a problem of the present invention resides in providing a new tool enabling the expression of genes in a plant, which should preferably not result in gene silencing when multiple transgenes are driven in a cell by the same promoter, a fact known to occur with promoters that are highly active.

The above problem has been solved by a nucleotide sequence as identified by nucleotides 1 to 1067 of SEQ ID. No. 1 or functional parts thereof.

According to another embodiment the present invention provides for the entire gene sequence of a rbcS gene (SEQ ID. No. 1) and the cDNA (SEQ. ID. No. 2) transcribed therefrom.

According to yet another embodiment the present invention provides for a rbcS polypeptide as identified by SEQ. ID. No 3, which forms part of the Rubisco.

In the figures,

FIG. 1 shows a Northern blot analysis of total RNA isolated from various coffee tissues and hybridized with the rbcS cDNA FIG. 2 shows a map indicating the promoter and the coding region of the rbcS gene FIG. 3 shows a Southern blot of *Coffee arabica* var. *Caturra* genomic DNA.

The promoter region of the present invention is embodied in several distinct forms. The promoter region may be represented by a nucleotide sequence identified by nucleotides No 1 to 1067 of SEQ ID. No. 1, or in case in a form, wherein the 3' end thereof has been modified such that an easy fusion with a gene of interest may be accomplished. This may e.g. be achieved by creating a restriction site at the 3' end of the promoter region. In addition, a restriction site may also be created within the coding region of the rbcS gene, so that upon inserting a foreign gene a fusion polypeptide will be synthesized. The DNA identified by nucleotides 1 to 1067 of the nucleic sequence SEQ ID No. 1 may be advantageously used by fusing it, completely or partially, with a gene of interest, while preserving the reading frame, and then by cloning the whole into an expression vector which is introduced into coffee, so as to allow the expression of the protein encoded by this gene in coffee leaves.

According to an embodiment the polypeptide to be linked to the rbcS promoter may be the rbcS polypeptide as such, so that upon introducing such a construct into a plant cell the present coffee rbcS gene will be expressed. Hence, according to an embodiment the present invention provides for a nucleotide sequence as identified by SEQ ID. No. 1 and the corresponding cDNA (SEQ ID. No. 2) and the polypeptide synthesized upon translation of said cDNA (SEQ ID. No. 3).

The promoter of the present invention may be utilized to produce any desired gene in a plant, preferably in coffee or also in cacao, tomato, chicory, soy. Since the promoter is strong and may be induced by light it represents a valuable tool for the expression of exogeneous genes in plants. Moreover, as could be shown the multiple use of said promoter in plant cells does not result in gene silencing.

Moreover, part of any nucleotide sequence according to the present invention or of their complementary strands, which is at least 10 bp in length, may be used as a primer to carry out a PCR or as probe to detect in vitro or to modify in vivo at least one gene of interest. Such a nucleotide sequence is preferably a sequence derived from nucleotides 51 to 596 of the nucleic sequence SEQ ID No. 2.

The invention also covers all the food, cosmetic or pharmaceutical products comprising all or part of the DNA, or of the recombinant proteins according to the invention. Persons skilled in the art are indeed capable, by means of oligonucleotide probes or of appropriate antibodies, of detecting their presence in very low quantities.

During the studies leading to the present invention the present inventors have isolated a novel polypeptide produced in higher amounts during conditions of light in coffee leaves and characterized that polypeptide. To this end, the polypeptide from coffee leaves has been identified by N-terminal sequencing following two-dimensional gel electrophoresis. A full-length rbcS cDNA has been cloned from a coffee leaf cDNA library as well as its corresponding gene. By PCR approaches, a genomic DNA fragment containing the promoter of this gene was isolated. Using the uidA reporter gene, this promoter was tested in transgenic tobacco to verify its specificity.

I. Identification of the ribulose-1,5-bisphosphate carboxylase/oxygenase from coffee leaves The total proteins were extracted from leaves of *Coffea arabica* of the Caturra variety.

To do this, coffee leaves were rapidly ground in liquid nitrogen, which were then reduced to a powder according to the method of Damerval et al. (Electrophoresis 7 (1986), 52–54,). The coffee proteins were then extracted from 10 mg of this powder which was solubilized in 100 µl of solution containing 3% w/v of CHAPS, 8.5 M urea, 0.15% w/v of DTT and 3% v/v of ampholyte support pH 3–10.

The mixture was then centrifuged at 13,000 g for 5 min and the supernatant, which contained the total proteins of the coffee beans, was recovered.

Proteins in the supernatant were then separated by two-dimensional gel electrophoresis. Initially, electrophoresis was performed on the basis of a pH gradient, using the Multiphore system (Amersham Pharmacia Biotech AB, Björkgatan 30, 75182 Upsula, Sweden). To do this, 50 µl of the supernatant was deposited on a re-hydrated immobilised pH gradient gel strip (Amersham Pharmacia Biotech) and the electrophoresis was performed according to the manufacturer instructions.

To separate the total proteins according to their molecular weights, a second SDS-PAGE electrophoresis was performed on the gels derived from the first electrophoresis step, using Bio-Rad equipment (Bio-Rad Laboratories, 2000 Alfred Nobel Drive, Hercules, Calif. 94547 USA) under standard conditions, according to the Laemmli method (Nature, 277 (1970), 680–688,). To do this, the gel strips derived from the one-dimensional electrophoresis were equilibrated with 5 ml/gel of Tris buffer containing 6 M urea, 30% v/v of glycerol, 2% w/v of SDS, 2% w/v of DTT and 2.5% w/v of iodoacetamide. The gel strips were then placed on the gels of the second SDS-PAGE electrophoresis, and the migration of the proteins was carried out in a Bio-Rad equipment at 40 mA and at a temperature of 12° C. for 9 h.

The gels thus produced were silver stained by the Bjellqvist et al. method (Electrophoresis, 14 (1993), 1357–1365).

The images were then analysed with the aid of a scanner (Scanner XRS 12CX, X-Ray Scanner Corporation, 4030 Spencer Street, Torrance, Calif. 90503 USA) and with the aid of the Bio Image program (Bio Image, 777 East Eisenhower Parkway, Suite 950, Ann Arbor, Mich. 48108, USA).

The proteins separated by two-dimensional electrophoresis were transferred onto PVDF membranes in a CAPS buffer, with the aid of a Bio-Rad Transblot Cell (Bio-Rad, USA) maintained at 420 mA and at a temperature of 4° C. for 1 h 30 min, and then they were stained with coomassie blue, according to the instructions of Applied Biosystems (Applied Biosystems Inc., 850 Lincoln Centre Drive, Foster City, Calif. 94404 USA).

After the transfer, the membranes were dried at room temperature, before storing them at 18° C. in plastic pouches.

Microsequencing of the N-terminal sequences of the protein blots was carried out with the aid of a sequencer of the Beckman LF 3000 type and of the Beckman Gold HPLC system (Beckman Instruments Inc., 250 Harbor Boulevard Box 3100, Fullerton, Calif. 92634 USA).

The two-dimensional electrophoretic profile, under denaturant conditions of *C. arabica* leaves showed that one protein having an apparent molecular weight of around 16 kDa and a isoelectric point of 6.1, was present in high amounts. By comparison with other two-dimensional electrophoretic profiles from non-photosynthetic tissues of *C. arabica*, e.g. endosperm of green coffee beans, somatic embryos (torpedo stage), the accumulation of this protein appears leaf-specific. The N-terminal sequence of this protein has been identified by Edman degradation.

II. Construction of the Coffee Leaf cDNA Library

Total messenger RNA was extracted, according to Rogers et al. (Plant Physiol Biochem, 37 (1999), 261–272), from young coffee leaves of *Coffea arabica* var. Caturra 2308, grown in greenhouse (temperature of approximately 25° C., 70% humidity and natural lighting). Leaves are finely ground in liquid nitrogen and at the end of the extraction, RNA was resuspended in sterile water and quantified by adsorption at 260 nm. Poly $(A)^+$ mRNA was purified from total RNA on an oligo-dT purification system (Qiagen INC, 9600 De Soto Avenue, Chatsworth, Calif., 913111 USA) and monitored for quality by electrophoresis and in vitro translation assays for mRNA.

The cDNA library was constructed as described in Rogers (supra), excepted that cDNA was ligated into pCR Script Cam SK (+) (Stratagene, 11011 North Torrey Pines Road, La Jolla, Calif. 92037, USA). The ligation mixture was used to transform *E. coli* XL10 Gold $Km^R$ (Stratagene, USA). Transformants were selected on LB (Luria-Bertani) agar containing 30 µg/ml of chloramphenicol and in presence of IPTG and X-Gal (Sambrook et al., A Laboratory Manual, Cold Spring Harbor N.Y. 1989).

III. Isolation of the rbcS Full-length cDNA

An RT-PCR experiment was carried out using 10 ng of total RNA from leaves as a template, in the presence of with AMV reverse transcriptase and Tfl DNA polymerase as described in the kit Access RT-PCR system (Promega Corporation, 2800 Woods Hollow Road, Madison, Wis. 53711 USA). The degenerate primers used were RBC1 (SEQ ID No. 6) and RBC3 (SEQ ID NO. 7). RBC1 was deduced from the N-terminal sequencing of the coffee polypeptide isolated as above (SEQ ID No. 4). In this case and by comparison with other RbcS proteins, the histidine in position 1 was corrected and replaced by a methionine and the undetermined residue in the fourth position was considered as a tryptophan (W). RBC3 is deduced from the amino acid sequence YWTMWK (SEQ ID No. 5) corresponding to a region highly conserved in other RbcS plant proteins. The PCR reaction (U.S. Pat. No. 4,683,195 and U.S. Pat. No. 4,683,202) was performed in a Robocycler (Stratagene, USA) for 50 cycles at 94° C. for 60 sec, 50° C. for 90 sec, and 68° C. for 2 min. followed by a final extension at 68° C. for 7 min. Under these conditions, only one PCR fragments of approximately 200 bp was observed after agarose gel electrophoresis and cloned in the vector pGEM-T easy (Promega, USA) as described by the furnisher. Its sequence analysis revealed that it corresponds effectively to a partial rbcS cDNA of 213 bp, flanked by the RBC1 and RBC3 primers at its extremities, and located between the nucleotides 234 and 446 of the sequence SEQ ID No.2.

The specific primers RBC11 (SEQ ID NO. 8) and RBC31 (SEQ ID NO. 9), which derived from RBC1 and RBC3, respectively, were synthesised and used to screen 300 individual E. coli clones harbouring a leaf cDNA by PCR. This reaction was carried out in a total volume of 50 µl containing 3 units of Taq DNA polymerase (Stratagene, USA), 50 mM KCl, 1.5 mM $MgCl_2$, 0.1 mg/ml gelatin, 0.2 mM of each dNTP, 0.25 µM primers and 10 mM Tris HCl pH 8.8. PCR reaction was performed using a Robocycler (Stratagene, USA) for 30 cycles at 94° C. for 60 sec, 65° C. for 75 sec, and 72° C. for 2 min. followed by a final extension at 72° C. for 7 min. Only one clone appeared positive.

IV. Analysis of the Coffee rbcS cDNA

This cDNA (934 bp) contained a 5' untranslated region of 50 bases and a 3' unstranslated region of 278 bases including a putative polyadenylation site (AATAAA) located 30 bases upstream of the polyA tail containing 62 adenosine residues. It also contained an open reading frame of 543 bases encoding for a protein of 181 amino acids presented in the sequence SEQ ID NO. 3. This protein has a theoretical molecular weight of about 20.4 Kda and a pI of 8.86 in its mature form. By comparison with its N-terminal sequence, which begins at the position 59 in the sequence SEQ ID NO. 3, the molecular weight of the processed form of this protein of about 15.6 Kda with a pI of 6.1 was deduced. These data were correlated with those estimated by 2D-gel electrophoresis, as described above.

V. Cloning of the rbcS Gene

In order to isolate the rbcS gene corresponding to the cDNA cloned before, two synthetic primers, designated RBC100 and RBC101, were designed to perform a PCR reaction using 50 ng of coffee genomic DNA as a template. This genomic DNA was purified according to the protocol described before (Paillard et al., Theor Appl Genet, 93 (1996), 41–47). RBC100 corresponds to the sequence SEQ. ID No. 10 and was located between the nucleotides 28 and 59 in the sequence SEQ ID No. 2.

RBC101 is located after the translated coding sequence, on the antisense strand of the nucleic sequence SEQ ID No. 2, between nucleotides 650 and 681. A PCR reaction was carried out as described above, for 45 cycles at 94° C. for 60 sec, 55° C. for 90 sec, and 72° C. for 4 min. followed by a final extension at 72° C. for 7 min. Following agarose gel electrophoresis of PCR products, only one band of approximately 1000 pb was detected, cloned into the pGEMT-easy vector according to recommendation of the furnisher (Promega, USA) and sequenced. Its analysis revealed that it corresponds to the rbcS gene which contains two short introns of 120 and 235 bp respectively located in the sequence SEQ ID No. 1, between the nucleotides 1229 and 1350 for the first and the nucleotides 1484 and 1720 for the second. Given the fact that this gene belongs to a multigene family, like observed in other plants (Dean et al. 1989), it will be called hereinafter rbcS1.

VI. Southern Hybridization Analysis

Coffee genomic DNA was purified according to the protocol described before (Paillard et al. Theor Appl Genet 93, 41–47, 1996). Genomic DNA (10 µg) was digested by restriction enzymes, and blotted onto a Nylon membrane as described previously (Southern, J Mol Biol 98, 503–517, 1975) and probed with the $^{32}$P-labeled 1-kb PCR product corresponding to the rbcS1 gene. Five restriction enzymes (DraI, HincII, HindIII, SspI and EcoRI) were used to cleave coffee genomic DNA. This DNA was hybridized with a probe corresponding to the 1kb rbcS1 gene isolated before after amplification of genomic DNA by the primers RBC100 (SEQ ID No. 10) and RBC101 (SEQ ID No. 11). This amplification product was purified on a Microcon 100 cartridge (Amicon INC, 72 Cherry Hill Drive, Beverly, Mass. 01915 USA) and 50 ng of this fragment were labeled by random primer extension with 50 µCi of [α-$^{32}$P]dCTP according to the Megaprime kit (Amersham, UK). Furthermore, the Nylon filter was prehybridized for 4 hrs at 65° C. in a solution containing 6×SSC, 1×Denhart (0.2% Ficoll, 0.2% polyvinylpyrrolidone, 0.2% BSA fraction TV) and 50 µg/ml of denatured salmon sperm DNA. It was then hybridized for 10 hrs at 65° C. in the same solution with the labeled probe and then it was washed for 30 min at 65° C. three times in the presence of, successively, 2×SSC-0.1% SDS, 1×SSC-0.1% SDS and 0.1×SSC-0.1% SDS.

Two bands were observed when coffee DNA was cut by DraI, HindIII and EcoRV enzymes whereas no restriction sites are present in the part of the rbcS1 gene hybridizing to the probe (FIG. 3). By comparison with the sequence SEQ ID No. 1, a signal greater than 1.75-kb was expected when coffee DNA was cut by DraI, which is effectively characterized by a strong hybridization at 2.25-kb in addition to a faint signal (1.3-kb). A strong hybridization was detected (0.8-kb) by the HincII digestion. It correspondeds probably to the expected rbcS1 gene fragment, which is internal to the probe. Again, a discrete signal at 1.5 kb was also revealed. One SspI site was present in the rbcS1 gene, leading theoretically to the detection of two fragments greater than 1.6 and 0.4 kb. Indeed, three hybridization bands of 0.9, 2.25 and 2.75 kb were observed. The same kind of analysis can also be done for the EcoRI digestion with two expected fragments greater than 1.45 and 0.55 kb and the presence of three bands at 2.3, 4.2 and 10 kb. Together, this analysis confirmed the existence of a rbcS gene family in coffee with some of them probably organized as a tandem.

VII. Expression of the rbcS Gene in Different Tissue of C. arabica

A Northern-blot experiment was carried out to analyze rbcS gene expression in different tissue harvested from Coffea arabica var. Caturra 2308, grown in greenhouse, i.e. leaves, roots, sterns, flowers as well as in green coffee beans at 35 weeks after flowering. To do this, 20 µg of total RNA were denatured for 15 min at 65° C. in 1×MOPS buffer (20 mM MOPS, 5 mM sodium acetate, 1 mM EDTA, pH 7) in the presence of formamide (50%) and formaldehyde (0.66 M final). They were then separated by electrophoresis. The total RNA was then transferred and fixed on a positively charged Nylon membrane according to the recommendations provided by the provider (Boehringer Mannheim, Del.). A probe, corresponding to 200 bp of the rbcS, was synthesized by a PCR reaction, using the RBC11 and RBC31 primers described before and the full-length rbcS previously cloned as a template. The fragment obtained after amplification was purified on a Microcon 100 cartridge (Amicon INC, 72 Cherry Hill Drive, Beverly, Mass. 01915 USA) and 50 ng of this fragment were labeled by random primer extension with 50 µCi of [α-$^{32}$P]dCTP according to the Megaprime kit (Amersham, UK). Furthermore, the Nylon filter was pre-hybridized for 4 hrs at 65° C. in a solution containing 6×SSC, 1×Denhart (0.2% Ficoll, 0.2% polyvinylpyrrolidone, 0.2% BSA fraction IV) and 50 µg/ml of denatured salmon sperm DNA. It was then hybridized for 10 hrs at 65° C. in the same solution with the labelled probe and then it was washed for 30 min at 65° C. three times in the presence of, successively, 2×SSC-0.1% SDS, 1×SSC-0.1% SDS and 0.1×SSC-0.1% SDS.

This analysis showed that the rbcS probe hybridized with only one class of mRNAs. The estimated size of which is approximately 900 bases, close to that of the length of the nucleic sequence SEQ ID No. 2. It also showed that rbcS-specific mRNAs are very abundant in the leaves whatever their age, slightly detectable in flowers but absent in other non-photosynthetic tissue tested such as in roots, mature grain, stems and somatic embryos (FIG. 1).

VIII. Isolation of the Promoter of the rbcS Gene of *Coffea arabica*

The promoter of the rbcS gene of *Coffea arabica* was isolated by several inverse PCRs according to the method of Ochman et al. (Genetics 120 (1988), 621–623). To do this, the nuclear DNA of *C. arabica*, (0.5 to 1 µg) was digested with several restriction enzymes, such as for example BstBI and NdeI, and then treated with phenol:chloroform (1:1) and precipitated for 12 hrs at −20° C. in the presence of sodium acetate 0.3 M final and ethanol (2.5 volumes). After centrifugation at 10,000 g for 15 min at 4° C., the DNA was treated as described before (WO 99/02688)

a) Inverse PCR Reaction No. 1

This first reaction was carried out using the synthetic oligonucleotide RBC102, having the nucleic sequence SEQ ID No. 12, and the oligonucleotide RBC104, having the nucleic sequence SEQ ID No. 13. This inverse PCR reaction was carried out in the presence of 50 ng of ligated genomic DNA as described before and was incubated for 45 cycles (94° C.-60 s, 65° C.-60s, 72° C.-4 min) followed by a final extension cycle at 72° C. for 7 min. A DNA fragment of around 600 bp was amplified and derived from the inverse PCR reaction on the genomic DNA initially digested with the restriction enzyme BstBI. This DNA was then cloned into the vector pGEMT-easy. Its sequence analysis revealed that it is contained approximately 350 bp upstream of the primer RBC102, corresponding to the nucleotides located between the nucleotides 731 and 1082 in the sequence SEQ ID No. 1.

b) Inverse PCR Reaction No. 2

To obtain the nucleic sequences located upstream of the BstBI restriction site corresponding to the nucleotides 732 to 737 of the sequence SEQ ID No. 1, another inverse PCR reaction was carried out using, this time, the synthetic oligonucleotides RBC401 and RBC400 deduced from the genomic DNA sequence previously cloned during the first inverse PCR reaction. RBC401 and RBC400 corresponded to the nucleic sequences SEQ ID No. 14 and SEQ ID No. 15, respectively. This inverse PCR reaction was carried out under conditions identical to those described for the inverse PCR reaction No. 1, with the proviso that the binding of the oligonucleotides was carried out at 60° C. A DNA fragment of 1 kb amplified from the genomic DNA initially digested with the restriction enzyme NdeI was observed following gel electrophoresis. It was treated as defined above and its sequence analysis revealed that it was contained around 890 bp upstream of the primer RBS401, corresponding to the nucleotides located between the positions 1 and 894 of the sequence SEQ ID NO. 1.

c) Cloning of the Genomic DNA Fragments

The inverse PCR experiments form chimeric linear molecules by combining noncontiguous DNA fragments in the genome with each other (Ochman et al., 1988). Moreover, measurements of mutation frequency showed that the Pfu DNA polymerase is approximately twelve times more accurate than Taq DNA polymerase, which reduced the probability of point mutations during PCR amplifications (Lundberg et al., Gene. 108 (1991), 1–6,). For these reasons, a PCR reaction was carried out on the native genomic DNA of *C. arabica* variety Caturra, in the presence of Pfu DNA polymerase. This reaction was carried out in the presence of 50 ng of genomic DNA, in a final volume of 50 µl containing 10 nM KCl, 6 mM $(NH_4)_2SO_4$, 20 mM Tris-HCl, pH 8.0, 0.1% Triton X-100, 2 MM $MgCl_2$, 10 µg/ml BSA, 0.2 mM of each dNTP, 3 units of Pfu DNA polymerase and 0.25 µM of the oligonucleotides RBC101 and RBC150. The oligonucleotide RBC101 is described above whereas the primer RBC150 (SEQ ID No. 16) is located on the sense strand of the nucleic sequence SEQ ID No. 2, and corresponds to the nucleotides 6 to 35. The reaction mixture was incubated for 35 cycles (94° C.-60 s, 55° C.-90 s, 72° C.-4 min) followed by a final extension cycle at 72° C. for 7 min.

Following this PCR, a single fragment of around 2 kb was obtained and cloned into the vector pCR-Script Cam SK (+) to give the vector pRBCS1. By sequencing, it was shown that this genomic DNA fragment corresponds to the sequence between oligonucleotides RBC 101 and RBC150. The DNA amplified during this PCR reaction was then used for the construction of the vectors, as described below. A schema summarizing these experiments is presented in FIG. 2.

IX. Construction of the Genetic Transformation Vector Necessary for the Functional Analysis of the rbcS Promoter The sequences located upstream of the translational start site (ATG in position 51 in the sequence SEQ ID No. 2), and corresponding to the first 1049 bases of the nucleic sequence SEQ ID No. 1, were analyzed in order to test their capacity for controlling the expression of the reporter gene uidA, in the leaves of transformed plants.

To do this, a construct was prepared in the binary transformation vector pBI101 (Clontech Laboratories Inc., 1020 East Meadow Circle, Palo Alto, Calif. 94303-4230 USA). This vector contains the reporter gene uidA, which encodes the 13-glucuronidase (GUS) and the bacterial gene nptII, which encodes neomycin phosphotransferase. The latter confers resistance to kanamycin in the transformed plants. These two genes were bordered by the right and left ends of the T-DNA of the plasmid pTiT37 of *Agrobacterium tume-* faciens (Bevan, Nucl. Acids Res. 12, 8711–8721, 1984) which define the DNA region capable of being transferred into the genome of plants infected with this bacterium.

The vector pBI101 was double-digested with the restriction enzymes HindIII and XbaI according to the protocol defined by the supplier (Promega, USA). Next, a DNA fragment containing the rbcS promoter was obtained by PCR reaction carried out with 5 ng of plasmid pRBCS1, in a volume of 50 µl containing 10 mM KCl, 6 mM $(NH_4)_2SO_4$, 20 mM Tris-HCl, pH 8, 0.1% Triton X-100, 2 mM $MgCl_2$, 0.2 mM of each dNTP, 10 µg/ml BSA, 0.25 µM of the synthetic oligonucleotides RBC150H3 and RBC102X1 corresponding, respectively, to the sequences SEQ ID No. 17 and SEQ ID No. 18. The reaction mixture was incubated for 30 cycles (94° C.-60 s, 55° C.-60 s, 72° C.-3 min) followed by a final extension cycle at 72° C. for 7 min. The PCR product amplified was cloned into the pCR-Script Cam SK (+) as described above to give the recombinant vector named pRBCS2. Then, this vector was digested by HindIII and XbaI restriction enzymes in order to purify the DNA fragment including the rbcS promoter region. This DNA was cloned in the vector pBI101 which had also been digested by HindIII and XbaI restriction enzymes, leading to a vector named pRBCS2. By this approach, a translational fusion between the first 8 amino acids of the coffee ribulose-1,5-bisphosphate carboxylase/oxygenase, and the N-terminal end of β-glucuronidase was obtained.

In the plasmid pBI101, the uidA reporter gene is silent because it lacks a promoter. In contrast thereto, this same gene is expressed in plants transformed with the vector pBI121 because it is under the control of the constitutive CaMV 35 S promoter (Jefferson et al., EMBO J., 6 (1987), 3901–3907). These two plasmids were used respectively as negative and positive controls for the expression of the reporter gene uidA.

X. Transformation and Regeneration of Nicotiana tabacum

The transformation of Nicotiana tabacum var. XHFD8 was carried out with the pRBCS2 vector described above, as well as pBI101 and pBI121, according to the protocol described by Horsch et al. (Plant Mol. Biol. Manuel, Gelvin, Schilperoort and Verma Eds, Kluwer Academic Publishers Dordrecht, Netherlands, A5 (1993), 1–9).

To do this, foliar discs of plantlets which are germinated in vitro were incubated for about 2 min. with a transformed stationary phase culture of Agrobacterium tumefaciens diluted in a 0.9% NaCl solution so as to obtain an OD measurement at 600 nm of between 0.2 and 0.3. They were then dried on 3MM paper (Whatmann) and incubated without selection pressure in a culture chamber on MS-stem medium (MS salts 4.3 g/l, sucrose 30 g/l, agar 8 g/l, myo-inositol 100 mg/l, thiamine 10 mg/l, nicotinic acid 1 mg/l, pyridoxine 1 mg/l, naphtalenacetic acid (ANA) 0.1 mg/l, benzyladenine (BA) 1 mg/l) (Murashige and Skoog, Physiol. Plant 15 (1962), 473–497).

3 days after, the discs were transferred onto MS medium supplemented with kanamycin (100 µg/ml) and with cefotaxime (400 µg/ml) in order to multiply the transformed cells so as to obtain calli. These discs were then subcultured every week on fresh "MS stem" medium.

After 21 to 28 days, the buds which germinate were cut from the calli and were subcultured on standard MS medium, i.e. a MS medium free of phytohormones, but supplemented with kanamycin (100 µg/ml) and cephotaxime (200 µg/ml). After rooting on a Petri dish, the plantlets were transplanted into earthenware pots in a substrate composed of peat and compost and then grown in a greenhouse at a temperature of 25° C. and with a photoperoid of 16 hrs. For each transformation experiment, 30 plantlets (R0 generation) were selected. All these plantlets proved to be morphologically normal and fertile. They were selfed and produced seeds (R1 generation).

XI. Analysis of the Genomic DNA of Tobacco Plants Transformed with Agrobacterium tumefaciens The genomic DNA of transgenic tobacco plants was extracted from the leaves according to the protocol described by Rogers and (Bendich Plant Mol. Biol. Manuel, Gelvin, Schilpoort and Verma Eds, Kluwer Academic Publishers Dordrecht, Netherlands, A6 (1993), 1–11,) and were subsequently analyzed by PCR and by molecular hybridization, according to the Southern-Blot technique.

The PCR reactions were carried out with 10 ng of DNA in a final volume of 50 µl containing 50 mM KCl, 10 mM Tris-HCl, pH 8.8, 1.5 mM $MgCl_2$, 0.1 mg/ml gelatin, 0.2 mM of each dNTP, 3 units of Taq DNA polymerase, 0.25 µM of the oligonucleotide BI104, having the sequence SEQ ID No. 19, and 0.25 µM of the oligonucleotide BI105, having the sequence SEQ ID No. 20. The oligonucleotide BI104 is located at 27 bp downstream of the BamHI site of the plasmid BI101 and the oligonucleotide BI105 is located at 73 bp upstream of the BamHI site of the plasmid pBI101. The PCR reactions were carried out over 30 cycles (94° C.-30 s, 54° C.-30 s, 72° C.-2 min) followed by a cycle of 7 min at 72° C. (final extension).

The DNA fragments amplified from transgenic tobacco plants transformed with the plasmids pBI101 (negative control), pBI121 (positive control) and pRBCS2 have molecular weights of about 280 bp, 1030 bp, and 1300 bp respectively. In all cases, it was concluded that the fragment initially cloned upstream of the reporter gene uidA is intact.

Ten micrograms of the DNA from tobacco plants transformed with Agrobacterium tumefaciens were digested with BamHI. Next, the restriction fragments obtained were separated by electrophoresis on an agarose gel (1%) and the DNA was transferred onto a Nylon filter, before hybridizsing it independently with a probe uidA and a probe nptII described in WO 99/02688. These two probes were purified and labeled (50 ng) by random primer extension with 50 µCi of $[\alpha-^{32}P]dCTP$ according to the Megaprime kit (Amersham International plc., Amersham Place, Little Chalfont, Buckinghamshire HP7 9NA, UK) protocol.

The hybridization profiles obtained for each probe were then compared so as to select the tobacco plants transformed with Agrobacterium tumefaciens that bad integrated into their genome a single non-rearranged copy of the T-DNA. The selection of these plants was also confirmed by the results of the analysis of the segregation of the kanamycin-resistance character, after germination in vitro on standard MS medium of the R1 seeds of these plants. Indeed, in this case, a ¾-¼ segregation of the kanamycin-resistance character was observed, which is compatible with the integration of the T-DNA at a single locus of the nuclear DNA.

XII. Study of the Coffee rbcS Promoter in Transgenic Tobacco Plants

This study was carried out on R0 generation plants.

The measurements of the GUS activity were carried out on the leaves and roots according to the method described by Jefferson et al. (1987), using MUG (methyl umbelliferyl glucuronide) as a substrate and by measuring, by fluorimetry, the appearance of MU (methylumbelliferone). To do this, the foliar explants (10 mg) and the seeds (about 40) were ground in the presence of sterile sand in 300 μl of extraction buffer (50 mM $Na_2HPO_4$, pH 7.0, 10 mM EDTA, 10 mM β-mercaptoethanol). The cellular debris was removed by centrifugation for 15 min at 4° C. and the soluble proteins in the supernatant was quantified by the Bradford method (Anal. Biochem. 72, 248–254, 1976) according to the protocol defined by Bio-Rad (USA) and using BSA as standard. The measurements of GUS activity was carried out in microtiter plates incubated at 37° C., using 1 μg of soluble proteins in 150 μl of reaction buffer (extraction buffer with 1 mM MUG). The measurements of fluorescence, expressed in pmol MU/min/mg of proteins was carried out at an excitation wavelength of 365 nm and an emission wavelength of 455 nm (FluoroskanII, Labsystem).

As shown in Table 1, no GUS activity was found in roots and leaves of WT (non-transformed plants) as well as in plants transformed by the pBI101 vector. As a positive control, similar levels of GUS activities are found in both tissue of tobacco plants transformed by pBI121 confirming the constitutive character of the 35S promoter. For 21 independent tobacco transformed by the pRBCS2 vector, GUS activities were exclusively found in leaves, ranging from 0.2 to 124 nmol MU $min^{-1}$ $mg^{-1}$ protein, whereas no GUS activity was found in the corresponding roots. For five of them, it was decided to analyze the effect of light on the control of the GUS reporter gene. Therefore, these plants were kept in dark conditions for 24 hours. After this period, their leaves were rapidly frozen in liquid nitrogen and tested for GUS expression at the protein (GUS activity) and nucleic level (northern-blotting). Measurements of GUS activities clearly showed a great reduction of this enzymatic activity in dark-grown leaves by a factor ranging from 2 to 40 (average factor reduction of 13) (cf. Table 1, below).

TABLE 1

| GUS activities in tobacco plants. | | | | |
|---|---|---|---|---|
| | Roots (R) | Leaves (L) | Leaves dark (LD) | n |
| WT | 0 | 0 | nd | 6 |
| pBI101 | 0 | 0 | nd | 4 |
| pBI121 | 3.62 (0.6–11) | 1.25 (0.3–3.2) | nd | 6 |
| pRBCS2 | 0 | 15.2 (0.2–124) | nd | 21 |
| pRBCS2[1] | 0 | 16.09 (1.45–52) | 1.25 (0–4) | 5 |

The fluorimetric assay for GUS activity was carried out as described by Jefferson et. al. (EMBO J., 6, 3901–3907, 1987). Soluble proteins were extracted from leaves and grains of self-fertilised TO tobacco plants in phosphate buffer (50 mM sodium phosphate pH 7, 10 mM $Na_2EDTA$, 40 mM 2 β-mercaptoethanol)without detergent. Either 1 or 4 μg of soluble protein were incubated with 1 mM MUG (4-methyl-umbelliferyl glucuronide) in a 200 μl final reaction mixture. Fluorescence was measured at 2-min intervals for 40 min with Fluoroskan II fluorimeter (Thermo Labsystenis Oy, Sorvaajankatu 15, P.O.Box 208, FIN-00811 Helsinki, Suomi). Fluorescence of a solution of 4-methylumbelliferone (MU) in reaction buffer was used as a standard.
GUS activity was measured in fresh light-grown leaves (L), 24 h dark-grown leaves (LD) and roots (R). Names of plasmids used are indicated as well as the number of transformants tested (n). Values indicated represent the average of GUS activity for several independent transformants (n) expressed as picomoles of 4-MU (methyl-umbelliferone) per mm per mg of total proteins. Values in brackets represent extreme values.
(nd): not determined.
[1] five transformants among 21 were tested.

This result was also confirmed by northern blotting, showing an important decrease of uidA-specific mRNA in leaves of dark-grown transformants by comparison to leaves of light-grown transformants. Together this result showed that the rbcS coffee promoter tested in transformed tobacco plants both conferred leaf-specific and light-regulation of gene expression in this plant. This may be explained by the fact that this promoter contains a TATA box-like element located 35 bp upstream of the 5' end of the cDNA as well as a CCAAT motif at around 80 bp upstream of the previous box. A more detailed analysis also revealed that this coffee sequence contains several Light-Responsive Elements (LRE) known to be essential for the photoregulation of gene expression in other plants.

The above results showed that the rbcS1 coffee promoter contains all the DNA sequences required to regulate gene expression in a tissue and light-specific manner and demonstrate that coffee DNA motifs are correctly recognized by the tobacco trans-acting factors.

The invention claimed is:

1. An isolated nucleotide sequence from nucleotide 1 to nucleotide 1067 of SEQ ID. No. 1 or a functional part thereof, wherein the functional part includes a promoter function.

2. An isolated nucleotide sequence identified by SEQ ID. No. 1 encoding a coffee rbcS protein.

3. An isolated nucleotide sequence identified by SEQ ID. No. 2 encoding a coffee rbcS protein.

4. A vector containing a nucleotide sequence according to claim 1.

5. An isolated polypeptide sequence as identified by SEQ ID. No. 3.

6. A method for expression of a gene in plants comprising the step of transfecting the plants with an expression vector comprising the gene under control of the nucleotide sequence from nucleotide 1 to nucleotide 1067 of SEQ ID NO:1 or a functional part thereof, wherein the functional part includes a promoter function.

7. The method of claim 6, wherein the plant is selected from the group consisting of coffee, tomato, cacao, soy and chicory.

8. A recombinant plant transformed with at least one nucleotide sequence according to claim 1.

9. The recombinant plant according to claim 8, which is selected from the group consisting of coffee, tomato, cacao, soy and chicory.

10. A vector containing a nucleotide sequence according to claim 2.

11. A vector containing a nucleotide sequence according to claim 3.

* * * * *